United States Patent [19]
Jeppesen et al.

[11] Patent Number: 6,015,813
[45] Date of Patent: Jan. 18, 2000

[54] HETEROCYCLIC COMPOUNDS AND THEIR PREPARATION AND USE

[75] Inventors: Lone Jeppesen, Virum; Per Sauerberg, Farum, both of Denmark

[73] Assignee: Novo Nordisk A/S, Bagsvaerd, Denmark

[21] Appl. No.: 09/057,207

[22] Filed: Apr. 8, 1998

Related U.S. Application Data

[60] Provisional application No. 60/044,242, Apr. 22, 1997, and provisional application No. 60/062,657, Oct. 8, 1997.

[30] Foreign Application Priority Data

Apr. 22, 1997 [DK] Denmark .................................. 0455/97
Sep. 29, 1997 [DK] Denmark .................................. 1114/97

[51] Int. Cl.⁷ ..................... A61K 31/505; A61K 31/445; C07D 417/14
[52] U.S. Cl. .......................... 514/256; 514/212; 514/216; 514/299; 514/305; 514/362; 514/342; 544/333; 546/112; 546/133; 546/268.7; 540/593; 540/601; 540/603; 548/135
[58] Field of Search ............................. 548/135; 546/112, 546/133; 544/333; 514/362, 305, 299, 256

[56] References Cited

U.S. PATENT DOCUMENTS

| | | | |
|---|---|---|---|
| 5,527,813 | 6/1996 | Sauerberg et al. | 514/361 |
| 5,914,338 | 6/1999 | Jeppesen et al. | 514/362 |

FOREIGN PATENT DOCUMENTS

WO 94/20496  9/1994  WIPO.
WO 97/40045 10/1997  WIPO.

OTHER PUBLICATIONS

Ward et al., "Novel Functional M1 Selective Muscarinic Agonists," J. Med. Chem., vol. 35, pp. 4011–4019, 1992.

Levine, "Controlled Trials of Inositol in Psychiatry," Eur. Neuropsychopharmacology, vol. 7, No. 2, MEDLINE abstract, May 1997.

*Primary Examiner*—Mukund J. Shah
*Assistant Examiner*—Ann M. Kessinger
*Attorney, Agent, or Firm*—Steve T. Zelson; Carol E. Rozek

[57] ABSTRACT

The present invention relates to therapeutically active azabicyclic compounds of formula I

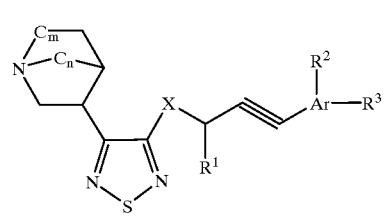

(I)

wherein X, $R^1$, $R^2$, $R^3$, Ar, m and n are defined in the description, a method of preparing the same and to pharmaceutical compositions comprising the compounds. The novel compounds are useful in treating a disease in the central nervous system caused by malfunctioning of the muscarinic cholinergic system.

23 Claims, No Drawings

HETEROCYCLIC COMPOUNDS AND THEIR PREPARATION AND USE

CROSS-REFERENCE TO RELATED APPLICATIONS

This application claims priority of U.S. provisional application No. 60/044,242 filed Apr. 22, 1997 and No. 60/062,657 filed Oct. 8, 1997 and of Danish application nos. 0455/97 filed Apr. 22, 1997 and 1114/97 filed Sep. 29, 1997, respectively, the contents of which are fully incorporated herein by reference.

FIELD OF THE INVENTION

The present invention relates to therapeutically active azabicyclic compounds, a method of preparing the same and to pharmaceutical or veterinary compositions comprising the compounds. The novel compounds are useful in treating a disease in the central nervous system caused by malfunctioning of the muscarinic cholinergic system.

BACKGROUND OF THE INVENTION

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic receptors in the forebrain and hippocampus still exist. Therefore cholinergic agonists are useful in the treatment of Alzheimer's disease, in halting progression of Alzheimer's disease, and in improving the cognitive functions of elderly people.

Compounds active at a muscarinic cholinergic receptor are also useful analgesic agents and therefore are useful in the treatment of severely painful conditions.

Furthermore, the compounds of this invention are useful in the treatment of glaucoma, psychosis, mania, bipolar disorder, schizophrenia or schizophreniform conditions, depression, bladder dysfunctions, anxiety, sleeping disorders, epilepsy, cerebral ischemia and gastrointestinal motility disorders.

WO 92/03433 and WO 94/20496 disclose therapeutically active azabicyclic compounds which are substituted by either a 1,2,5-thiadiazole or a 1,2,5-oxadiazole ring system. The compounds disclosed therein are active at the muscarinic cholinergic receptors.

Within the muscarinic cholinergic pharmacology five subtypes of muscarinic cholinergic receptors exist which are $M_1$ through $M_5$. Some muscarinic cholinergic receptor active compounds are associated with side effects attributed to undesired modulation of the muscarinic cholinergic receptors.

Therefore, new compounds having muscarinic cholinergic activity are desired which have a better combination of receptor subtype efficacy, potency and selectivity.

The presently claimed compounds have a surprisingly good combination of $M_1$ receptor efficacy, potency and selectivity.

SUMMARY OF THE INVENTION

It is an object of the invention to provide new muscarinic cholinergic compounds.

The novel compounds of the invention are heterocyclic compounds having the formula I

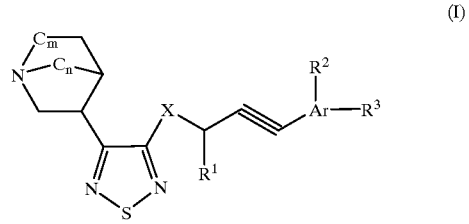

wherein

X is oxygen or sulphur; and $R^1$ is hydrogen, straight or branched $C_{1-5}$-alkyl, straight or branched $C_{2-5}$-alkenyl, straight or branched $C_{2-5}$-alkynyl or straight or branched $C_{4-5}$-alkenynyl, each of which is optionally substituted with one or more halogen(s); and $R^2$ and $R^3$ are independently hydrogen, halogen, CN, $NO_2$, $CF_3$, $OCF_3$, $C_{1-3}$-alkyl, $C_{1-3}$-alkoxy or $C_{1-3}$-alkylthio, wherein $C_{1-3}$-alkyl, $C_{1-3}$-alkoxy and $C_{1-3}$-alkylthio are optionally substituted with one or more halogen(s), cyano, amino or nitro; and Ar is phenyl, thienyl, pyridyl, pyrimidinyl, thiazolyl or furyl; and n is 0, 1 or 2; and m is 0, 1 or 2; or a pharmaceutically acceptable salt or solvate thereof.

As used herein, the term "halogen" means F, Cl, Br and I. Especially preferred halogens include Cl, Br and F.

The term "$C_{1-n'}$-alkyl" wherein n' can be from 2 through 5, as used herein, represent a branched or straight alkyl group having from one to the specified number of carbon atoms. Typical $C_{1-4}$-alkyl groups include, but are not limited to, methyl, ethyl, n-propyl, iso-propyl, butyl, iso-butyl, sec-butyl, tert-butyl and the like.

The term "$C_{2-n'}$-alkenyl" wherein n' can be from 3 through 5, as used herein, represents an olefinically unsaturated branched or straight group having from 2 to the specified number of carbon atoms and at least one double bond. Examples of such groups include, but are not limited to, 1-propenyl, 2-propenyl, 1,3-butadienyl, 1-butenyl, pentenyl, and the like.

The term "$C_{2-n'}$-alkynyl" wherein n' can be from 3 through 5, as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The term "$C_{4-5}$-alkenynyl" as used herein, represent an unsaturated branched or straight hydrocarbon group having from 4 to 5 carbon atoms and both at least one double bond and at least one triple bond. Examples of such groups include, but are not limited to, 1-penten4-yne, 3-penten-1-yne and the like.

The term "$C_{1-3}$-alkoxy" as used herein, alone or in combination, refers to a straight or branched monovalent substituent comprising a $C_{1-3}$-alkyl group linked through an ether oxygen having its free valence bond from the ether oxygen and having 1 to 3 carbon atoms. Examples of such groups include, but are not limited to, e.g. methoxy, ethoxy, propoxy, isopropoxy and the like.

The term "$C_{1-3}$-alkylthio" as used herein, alone or in combination, refers to a straight or branched monovalent substituent comprising a $C_{1-3}$-alkyl group linked through a divalent sulfur atom having its free valence bond from the sulfur oxygen and having 1 to 3 carbon atoms. Examples of such groups include, but are not limited to, e.g. methylthio, ethylthio, propylthio, isopropylthio, butylthio and the like.

As used herein, the phrase "one or more selected from" shall more preferably refer to From 1–3 substituents. The term shall further preferably refer to from 1–2 substituents.

In a preferred embodiment, the present invention is concerned with compounds of formula I wherein X is oxygen.

In another preferred embodiment, the present invention is concerned with compounds of formula I wherein X is sulfur.

In another preferred embodiment, the present invention is concerned with compounds of formula I wherein $R^1$ is hydrogen.

In a further preferred embodiment, the present invention is concerned with compounds of formula I wherein $R^1$ is straight or branched $C_{1-5}$-alkyl, preferably straight or branched $C_{1-3}$-alkyl.

In a further preferred embodiment, the present invention is concerned with compounds of formula I wherein $R^1$ is isopropyl.

In a further preferred embodiment, the present invention is concerned with compounds of formula I wherein $R^2$ and $R^3$ are halogen.

In a further preferred embodiment, the present invention is concerned with compounds of formula I wherein Ar is phenyl or thienyl.

In a further preferred embodiment, the present invention is concerned with compounds of formula I wherein m is 1 or 2.

In a further preferred embodiment, the present invention is concerned with compounds of formula I wherein n is 1 or 2.

It is to be understood that the invention extends to each of any of the stereoisomeric forms of the compounds of the present invention as well as the pure diastereomeric, pure enantiomeric, and racemic forms of the compounds of this invention.

The starting materials for the illustrated process are, if nothing else mentioned, commercially available or may be prepared using methods known to the skilled artisan.

The invention also relates to methods of preparing the above mentioned compounds, comprising:

a) The propargyl side chains can be prepared by standard cross coupling methods using iodine or bromine substituted aromates and propargylalcohols in the presence of a palladium catalyst e.g.:

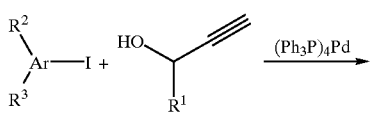

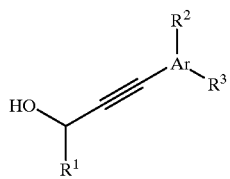

wherein Ar, $R^1$, $R^2$ and $R^3$ have the meanings defined above which alcohol can be reacted with an azabicyclic 1,2,5-thiadiazole under basic conditions

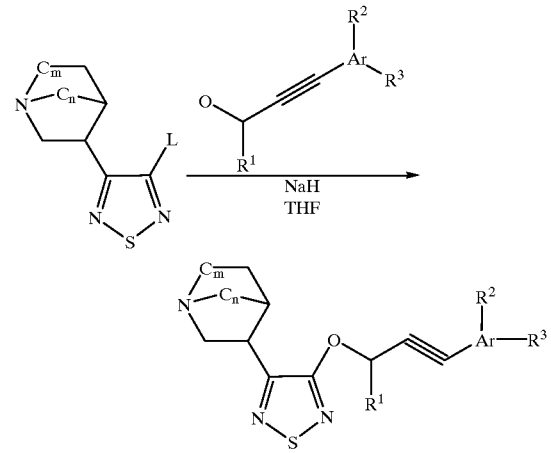

wherein L is a leaving group e.g chlorine or $SO_2R$, wherein R is alkyl or phenyl and Ar, $R^1$, $R^2$, $R^3$, n and m have the meanings defined above; or b) compounds wherein X is S can be synthesized by displacing the leaving group L with sulfur e.g. using NaSH, and then alkylating on the sulfur atom with P-propargylalcohol, wherein O—P is a leaving group e.g O—$SO_2R$ or O— "Mitsunobu", wherein R has the meaning defined above,

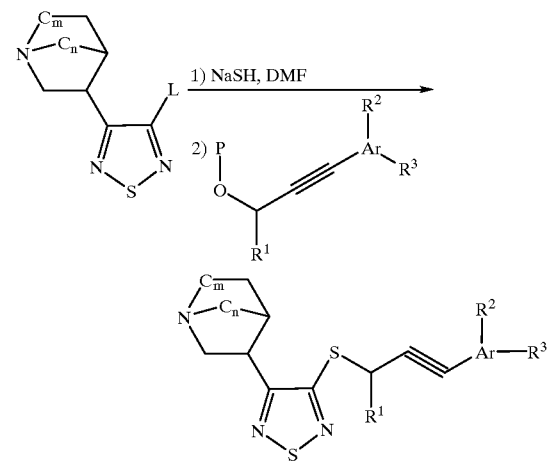

and wherein Ar, $R^1$, $R^2$, $R^3$, n and m have the meanings defined above.

As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

The invention further provides a formulation comprising a compound of formula I and one or more pharmaceutically acceptable diluents, carriers or excipients therefor.

The invention provides a method for treating a condition associated with a malfunction of the cholinergic muscarinic receptor system. Such conditions which may be treated using a compound of this invention include, but are not limited to Alzheimer's Disease, cognitive dysfunction, severely painful conditions, glaucoma, psychosis, schizophrenia, bladder dysfunction, anxiety, sleep disorders, and other such conditions associated with the modulation of a muscarinic receptor.

As used herein the term "treating" includes prophylaxis of a physical and/or mental condition or amelioration or elimination of the developed physical and/or mental condition once it has been established or alleviation of the characteristic symptoms of such condition.

As used herein the term "malfunctioning of the muscarinic cholinergic system" shall have the meaning accepted by the skilled artisan. For example the term shall refer to, but is not in any way limited to conditions such as glaucoma, psychosis, schizophrenia or schizophreniform conditions, depression, sleeping disorders, epilepsy and gastrointestinal motility disorders. Other such conditions include Alzheimer's disease and incontinence.

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

The pharmacological properties of the compounds of the invention can be illustrated by determining the $M_1$ efficacy and potency of the compounds of the present invention in A9 L-$m_1$ cells.

IP hydrolysis in A9 L cells cloned with the genetic $m_1$ muscarinic receptor: A9 L cells transfected with human and rat $m_1$ muscarinic receptors (Dörje et al., 1991; Jones et al., 1988), were cultured to confluence in 75-ml flasks containing Dulbecco's modified essential media. Cells were prelabeled with 1 $\mu$Ci/ml of myo(2-[$^3$H]inositol (Amersham Inc., 16.3 Ci/mmol) for 48 hr before assaying. On the day of assay, cells were detached using a 30-sec exposure to 0.25% trypsin in 1 mM EDTA. The cells were collected by centrifugation (300×g for 5 min) and resuspended in oxygenated HEPES buffer containing 10 mM LiCl (NaCl 142 mM, KCl 5.6 mM, CaCl$_2$ 2.2 mM, MgCl$_2$ 1 mM, NaHCO$_3$ 3.6 mM, D-glucose 5.6 mM and Na$^+$ HEPES 30 mM, pH 7.4). Cells were incubated at 37° C. for 45 min in the presence of varying concentrations of test compounds. Total IP hydrolysis was determined using the method of Schoepp and Johnson (1988). Data are expressed as the percentage of total [$^3$H]IP accumulated in the presence of 100 $\mu$M carbachol stimulation. Half-maximal (EC$_{50}$) values were determined from the mean (±S.D.) of seven point curves determined from three separate experiments.

Test results obtained by testing some compounds of the present invention will appear from the following table 1:

TABLE 1

| | A9 L-$m_1$ cells | |
|---|---|---|
| Compound no | % PI (efficacy) | EC$_{50}$, nM |
| 1 | 80 | 210 |
| 2 | 74 | 1800 |
| 3 | 81 | 95 |
| 4 | 77 | 159 |
| 5 | 73 | 42 |
| 7 | 108 | 380 |
| 8 | 91 | 670 |
| 9 | 68 | 38 |
| 10 | 57 | 75 |
| 11 | 64 | 98 |
| 13 | 100 | 0.7 |
| 16 | 56 | 14 |
| 20 | 98 | 1 |
| 21 | 67 | 105 |
| 24 | 105 | 300 |
| 25 | 69 | 210 |
| 26 | 93 | 280 |
| 27 | 79 | 187 |
| 28 | 97 | 22 |
| 30 | 82 | 20 |
| 31 | 108 | 26 |
| 39 | 105 | 0.2 |
| 40 | 102 | 0.5 |
| 41 | 100 | 2 |
| 42 | 99 | 12 |
| 43 | 85 | 9 |
| 44 | 81 | 32 |
| 45 | 66 | 8 |
| 47 | 102 | 102 |
| 48 | 96 | 7 |
| 49 | 100 | 0.7 |
| 50 | 101 | 2 |
| 53 | 97 | 13 |
| 54 | 102 | 224 |
| Carbachol | 99 | 4600 |
| oxotremorine | 88 | 16300 |

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, depot, subcutaneous, intravenous, intraurethral, intramuscular, intranasal, ophthalmic solution or an ointment, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

A typical tablet, appropriate for use in this method, may be prepared by conventional tabletting techniques and contains:

| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

The compounds according to this invention may be suitable for administration to an animal. Such animals include both domestic animals, for example livestock, laboratory animals, and household pets, and non-domestic animals such as wildlife. More preferably, the animal is a vertebrate. Most preferably, a compound according to this invention shall be administered to a mammal. It is especially preferred that the animal is a domestic mammal or a human. The most preferred mammal is a human. For such purposes, a compound of this invention may be administered as a feed additive or in bulk form.

The invention will now be described in further detail with reference to the following examples. The examples are provided for illustrative purposes, and are not to be construed as limiting the scope of the invention in any way.

The absolute configuration is not known for all of the following examples. The use of α in the nomenclature refers to the starting material having (+) configuration, whereas the use of β refers to the starting material having (−) configuration.

EXAMPLE 1

Endo (+−) 3-(3-(3-Phenyl-2-propyn-1-yloxy)-1,2,5-thiadiazol-4-yl)-1-azabicyclo[2.2.1]heptane.(+)-tartrate To a mixture of sodium hydride (60% in mineral oil, 0.63 g, 15 mmol) in THF (50 ml) was added 3-phenyl-2-propyn-1-ol (0.62 g, 0.47 mmol) at room temperature and the reaction mixture was stirred for 1 hour. After cooling to 0° C., endo (+−)3-(3-propylsulfonyl-1,2,5-thiadiazol-4-yl)-1-azabicyclo[2.2.1]heptane (WO 94/20496) (0.48 g, 1.66 mmol) was added. The reaction mixture was stirred for 5 hours at room temperature and at 5° C. overnight. Water (50 ml) was added and the mixture was extracted with ether (3×100 ml). The ether phases were evaporated and the residue was dissolved in 1N hydrochloric acid (20 ml). The water phase was washed with ether (100 ml), made basic with 25% aqueous ammonia and then extracted with ether (2×100 ml). The ether phases were dried and evaporated to give crude product. Purification on column chromatography eluting with ethyl acetate:methanol:25% aq.NH$_3$ (2:1:2%) gave the desired free base product as an oil. Crystallization with L-(+)-tartaric acid from isopropanol gave the title compound in 300 mg (39%) yield. Mp. 122–125° C. Compound 1.

The following compound was made in the same manner using the appropriate alcohol:

Endo (+−)3-(3-(3-(4-Fluorophenyl)-2-propyn-1-yloxy)-1,2,5-thiadiazol-4-yl)-1-azabicyclo[2.2.1]heptane, (+)-tartrate. Mp. 130–132° C. Compound 2.

EXAMPLE 2

Endo (α)-3-(3-(3-(4-Fluorophenyl)-2-propyn-1-yloxy)-1,2,5-thiadiazol-4-yl)-1-azabicyclo[2.2.1]heptane, (+)-tartrate To a mixture of sodium hydride (60% in mineral oil, 0.5 g, 12.5 mmol) in THF (50 ml) was added 3-(4-fluorophenyl)-2-propyn-1-ol (0.42 g, 2.8 mmol) at room temperature and the reaction mixture was stirred for 1 hour. After cooling to 0° C., endo (+)3-(3-propylsulfonyl-1,2,5-thiadiazol-4-yl)-1-azabicyclo[2.2.1]heptane (WO 94/20496) (0.47 g, 1.66 mmol) was added. The reaction mixture was stirred for 5 hours at room temperature and at 5° C. overnight. Water (50 ml) was added and the mixture was extracted with ether (3×100 ml). The ether phases were evaporated and the residue was dissolved in 1N hydrochloric acid (20 ml). The water phase was washed with ether (100 ml), made basic with 25% aqueous ammonia and then extracted with ether (2×100 ml). The ether phases were dried and evaporated to give crude product (0.41 g). Purification on column chromatography eluting with ethyl acetate:methanol:25% aq.NH$_3$ (2:1:2%) gave the desired free base product as an oil.

Crystallization with L-(+)-tartaric acid (204 mg, 1.36 mmol) from isopropanol gave the title compound in 575 mg (75%) yield. Mp. 141–142° C. Compound 3.

The following compounds were made in exactly the same manner using the appropriate alcohol:

Endo (α)-3-(3-(3-Phenyl-2-propyn-1-yloxy)-1,2,5-thiadiazol-4-yl)-1-azabicyclo[2.2.1]heptane, (+)-tartrate. Mp. 127–130° C. Compound 4.

Endo (α)-3-(3-(3-(3-Methoxyphenyl)-2-propyn-1-yloxy)-1,2,5-thiadiazol-4-yl)-1-azabicyclo[2.2.1]heptane, (+)-tartrate. Mp. 139–141° C. Compound 5.

Endo (α)-3-(3-(3-(4-Chlorophenyl)-2-propyn-1-yloxy)-1,2,5-thiadiazol-4-yl)-1-azabicyclo[2.2.1]heptane, (+)-tartrate. Mp. 163–164° C. Compound 6.

Endo (α)-3-(3-[3-(3-Thienyl)-2-propyn-1-yloxy]-1,2,5-thiadiazol-4-yl)-1-azabicyclo[2.2.1]heptane, (+)-tartrate. Mp. 141.5–143° C. Compound 7.

Endo (α)-3-(3-(3-(2-Thienyl)-2-propyn-1-yloxy)-1,2,5-thiadiazol-4-yl)-1-azabicyclo[2.2.1]heptane, (+)-tartrate. Mp. 113–115° C. Compound 8.

Endo (α)-3-(3-(3-(3,5-Difluorophenyl)-2-propyn-1-yloxy)-1,2,5-thiadiazol-4-yl)-1-azabicyclo[2.2.1]heptane, (+)-tartrate. Mp. 158–160° C. Compound 56.

Endo (α)-3-(3-(3-(3-Chloro-5-fluorophenyl)-2-propyn-1-yloxy)-1,2,5-thiadiazol-4-yl)-1-azabicyclo[2.2.1]heptane, (+)-tartrate. Mp. 120–121° C. Compound 57.

EXAMPLE 3

Endo (β)-3-(3-(3-(4-Fluorophenyl)-2-propyn-1-yloxy)-1,2,5-thiadiazol-4-yl)-1-azabicyclo[2.2.1] heptane, (−)-tartrate To a mixture of sodium hydride (60% in mineral oil, 0.63 g, 15 mmol) in THF (50 ml) was added 3-(4-fluorophenyl)-2-propyn-1-ol (0.70 g, 4.7 mmol) at room temperature and the reaction mixture was stirred for 1 hour. After cooling to 0° C., endo (−)3-(3-propylsulfonyl-1,2,5-thiadiazol-4-yl)-1-azabicyclo[2.2.1]heptane (WO 94/20496) (0.48 g, 1.66 mmol) was added. The reaction mixture was stirred for 5 hours at room temperature and at 5° C. overnight. Water (50 ml) was added and the mixture was extracted with ether (3×100 ml). The ether phases were evaporated and the residue was dissolved in 1N hydrochloric acid (20 ml). The water phase was washed with ether (100 ml), made basic with 25% aqueous ammonia and then extracted with ether (2×100 ml). The ether phases were dried and evaporated to give crude product (480 mg). Crystallization with D-(−) tartaric acid (240 mg, 1.6 mmol) from isopropanol gave the title compound in 450 mg (57%) yield. Mp. 85–88° C. Compound 9.

The following compounds were made in the same manner using the appropriate alcohol and appropriate acid:

Endo (β)-3-(3-(3-(3-Methoxyphenyl)-2-propyn-1-yloxy)-1,2,5-thiadiazol-4-yl)-1-azabicyclo[2.2.1]heptane, (−)-tartrate. Mp. 124–127° C. Compound 10.

Endo (β)-3-(3-(3-Phenyl-2-propyn-1-yloxy)-1,2,5-thiadiazol-4-yl)-1-azabicyclo[2.2.1]heptane, (+)-tartrate. Mp. 150–153° C. Compound 11.

Endo (β)-3-(3-(3-(3-Furyl)-2-propyn-1-yloxy)-1,2,5-thiadiazol-4-yl)-1-azabicyclo[2.2.1]heptane, (−)-tartrate. Mp. 129–131° C. Compound 58.

Endo (β)-3-(3-(3-(3-Cyanophenyl)-2-propyn-1-yloxy)-1,2,5-thiadiazol-4-yl)-1-azabicyclo[2.2.1]heptane, (−)-tartrate. Mp. 118–120° C. Compound 59.

Endo (β)-3-(3-(3-(3-Trifluoromethoxyphenyl)-2-propyn-1-yloxy)-1,2,5-thiadiazol-4-yl)-1-azabicyclo[2.2.1]heptane, (+)-tartrate. Mp. 54–55° C. Compound 60.

Endo (β)-3-(3-(3-(3-Chlorophenyl)-2-propyn-1-yloxy)-1,2,5-thiadiazol-4-yl)-1-azabicyclo[2.2.1]heptane, (−)-tartrate. Mp. 138–140° C. Compound 61.

Endo (β)-3-(3-(3-(3,5-Dichlorophenyl)-2-propyn-1-yloxy)-1,2,5-thiadiazol-4-yl)-1-azabicyclo[2.2.1]heptane, (−)-tartrate. Mp. 103–105° C. Compound 62.

Endo (β)-3-(3-(3-(3,5-Difluorophenyl)-2-propyn-1-yloxy)-1,2,5-thiadiazol-4-yl)-1-azabicyclo[2.2.1]heptane, (−)-tartrate. Mp. 158–160° C. Compound 63.

Endo (β)-3-(3-(3-(3-Bromophenyl)-2-propyn-1-yloxy)-1,2,5-thiadiazol-4-yl)-1-azabicyclo[2.2.1]heptane, (−)-tartrate. Mp. 75–77° C. Compound 64.

Endo (β)-3-(3-(3-(3-Fluorophenyl)-2-propyn-1-yloxy)-1,2,5-thiadiazol-4-yl)-1-azabicyclo[2.2.1]heptane, (−)-tartrate. Mp. 120–122° C. Compound 65.

Endo (β)-3-(3-(3-(3-Chloro-5-fluorophenyl)-2-propyn-1-yloxy)-1,2,5-thiadiazol-4-yl)-1-azabicyclo[2.2.1]heptane, (−)-tartrate. Mp. 101–103° C. Compound 66.

Endo (β)-3-(3-(3-(3-Bromo-5-fluorophenyl)-2-propyn-1-yloxy)-1,2,5-thiadiazol4-yl)-1-azabicyclo[2.2.1]heptane, (−)-tartrate. Mp. 137–138° C. Compound 67.

Endo (β)-3-(3-(3-(5-Chloro-2-thienyl)-2-propyn-1-yloxy)-1,2,5-thiadiazol-4-yl)-1-azabicyclo[2.2.1]heptane, (−)-tartrate. Mp. 139–141° C. Compound 68.

EXAMPLE 4

Endo (α)-3-(3-Phenyl-2-propyn-1-ylthio)-1,2,5-thiadiazol-4-yl)-1-azabicyclo[2.2.1]heptane, (+)-tartrate Endo (+)-3-(3-propylsulfonyl-1,2,5-thiadiazol-4-yl)-1-azabicyclo[2.2.1]heptane (WO 94/20496) (0.4 g, 1.4 mmol) and sodium hydrosulfide monohydrate (0.27 g, 3.8 mmol) were dissolved in dry DMF (50 ml) and the reaction mixture was refluxed at 100° C. for 3 hours (or to completion of reaction). After cooling to 0° C., potassium carbonate (0.76 g, 5.6 mmol) and 3-phenyl-2-propyn-1-yl methylsulfonate (0.51 g, 2.4 mmol) were added. The reaction mixture was stirred at room temperature for 4 hours (or to completion of reaction), after which 1N hydrogen chloride was added to pH 2. The aqueous phase was first washed with ether (2×50 ml), then potassium carbonate was added to pH>10 and finely the water phase was extracted with ether (2×100 ml). The combined and dried ether phases were evaporated and the residue (0.4 g) was crystallized with L-(+)-tartaric acid (0.2 g, 1.3 mmol) from isopropanol to give the title compound in 0.54 g yield (82%). Mp. 170–172° C. Compound 12.

The following compounds were made in exactly the same manner using the appropriate methylsulfonate:

Endo (α)-3-(3-(3-(4-Chlorophenyl)-2-propyn-1-ylthio)-1,2,5-thiadiazol-4-yl)-1-azabicyclo[2.2.1]heptane, (+)-tartrate. M.p.183–186° C. Compound 69.

Endo (α)-3-(3-(3-(3,5-Difluorophenyl)-2-propyn-1-ylthio)-1,2,5-thiadiazol-4-yl)-1-azabicyclo[2.2.1]heptane, (+)-tartrate. M.p.150–151° C. Compound 70.

Endo (α)-3-(3-(3-(3-Chloro-5-fluorophenyl)-2-propyn-1-ylthio)-1,2,5-thiadiazol-4-yl)-1-azabicyclo[2.2.1]heptane, (+)-tartrate. M.p.118–119° C. Compound 71.

EXAMPLE 5

Exo (+−)3-(3-(3-Phenyl-2-propyn-1-yloxy)-1,2,5-thiadiazol-4-yl)-1-azabicyclo[2.2.1]heptane, (+)-tartrate To a mixture of sodium hydride (60% in mineral oil, 0.63 g, 15 mmol) in THF (50 ml) was added 3-phenyl-2-propyn- 1-ol (0.46 g, 3.5 mmol) at room temperature and the reaction mixture was stirred for 1 hour. After cooling to 0° C., exo (+−)3-(3-propylsulfonyl-1,2,5-thiadiazol-4-yl)-1-azabicyclo[2.2.1]heptane (WO 94/20496) (0.40 g, 1.4 mmol) was added. The reaction mixture was stirred for 5 hours at room temperature and at 5° C. overnight. 1N hydrogen chloride (100 ml) was added and the mixture was washed with ether (100 ml). 25% ammonia was added to the water phase to pH>10 and then extracted with ether (2×100 ml). The combined and dried ether phases were evaporated to give an oil (0.39 g). Crystallization with L-(+)-tartaric acid (0.21 g, 1.4 mmol) from isopropanol gave the title compound in 0.51 g (80%) yield. Mp. 159–162° C. Compound 13.

The following compounds were made in exactly the same manner using the appropriate alcohol:

Exo (+−)3-(3-(1-(3-Methoxyphenyl)-4-methyl-1-pentyn-3-yloxy)-1,2,5-thiadiazol-4-yl)-1-azabicyclo[2.2.1]heptane, (+)-tartrate. Mp. 134–137° C. Compound 14.

Exo (+−)3-(3-(1-(4-Chlorophenyl)-4-methyl-1-pentyn-3-yloxy)-1,2,5-thiadiazol-4-yl)-1-azabicyclo[2.2.1]heptane, (+)-tartrate. Mp. 146–147° C. Compound 15.

Exo (+−)3-(3-(1-(3-Thienyl)-4-methyl-1-pentyn-3-yloxy)-1,2,5-thiadiazol-4-yl)-1-azabicyclo[2.2.1]heptane, (+)-tartrate. Mp. 133–138° C. Compound 16.

EXAMPLE 6

Exo (+−)3-(3-(4-Chlorophenyl)-2-propyn-1-ylthio)-1,2,5-thiadiazol-4--yl)-1-azabicyclo[2.2.1]heptane, (+)-tartrate Exo (+−)3-(3-propylsulfonyl-1,2,5-thiadiazol-4-yl)-1-azabicyclo[2.2.1]heptane (WO 94/20496) (0.275 g, 0.95 mmol) and sodium hydrosulfide monohydrate (0.21 g, 2.8 mmol) were dissolved in dry DMF (35 ml) and the reaction mixture was refluxed at 100° C. for 3 hours (or to completion of reaction). After cooling to 0° C., potassium carbonate (0.5 g, 3.7 mmol) and 3-(4-chlorophenyl)-2-propyn-1-yl methyl sulfonate (0.41 g, 1.67 mmol) were added. The reaction mixture was stirred at room temperature for 4 hours (or to completion of reaction), after which 1N hydrogen chloride was added to pH 2. The aqueous phase was first washed with ether (2×50 ml), then 25% ammonia was added to pH>10 and finely the water phase was extracted with ether (2×100 ml). The combined and dried ether phases were evaporated and the residue was crystallized with L-(+)-tartaric acid from isopropanol and ether to give the title compound in 40 mg yield. Mp. 188–190° C. Compound 17.

EXAMPLE 7

(3S)3-(3-(3-(4-Chlorophenyl)-2-propyn-1-yloxy)-1,2,5-thiadiazol-4-yl)-1-azabicyclo[2.2.2]octane, (+)-tartrate To a mixture of sodium hydride (60% in mineral oil, 0.72 g, 18 mmol) in THF (50 ml) was added 3-(4-chlorophenyl)-2-propyn-1-ol (0.55 g, 3.3 mmol) at 0° C. The reaction was stirred at 0° C. for 1 hour and then (3S)3-(3-butylsulfonyl-1,2,5-thiadiazol-4-yl)-1-azabicyclo[2.2.2]octane (Chirality, 1997, in press.) (0.50 g, 1.6 mmol) was added. The reaction mixture was stirred for 18 hours at room temperature. 1 N hydrogen chloride (75 ml) was added and the reaction mixture was washed with ether (2×50 ml). The water phase was made basic (pH>10) with potassium carbonate and then extracted with ether (3×100 ml). The combined ether phases were dried and evaporated. The residue was purified by column chromatography using ethyl acetate/methanol/25% ammonia (3:1:1%) as eluent. The product was crystallized with L-(+)-tartaric acid from isopropanol to give the title compound in 310 mg (54%) yield. Mp. 158–163° C. Compound 18.

The following compounds were made in exactly the same manner using the appropriate alcohol:

(3S)3-(3-(3-(3-Chlorophenyl)-2-propyn-1-yloxy)-1,2,5-thiadiazol-4-yl)-1-azabicyclo[2.2.2]octane, (+)-tartrate. Mp. 144–146° C. Compound 19.

(3S)3-(3-(1-(4-Chlorophenyl)-4-methyl-1-pentyn-3-yloxy)-1,2,5-thiadiazol-4-yl)-1-azabicyclo[2.2.2]octane, (+)-tartrate. Mp. (75–128)° C. Compound 72.

(3S)3-(3-(1-(3-Chlorophenyl)-4-methyl-1-pentyn-3-yloxy)-1,2,5-thiadiazol-4-yl)-1-azabicyclo[2.2.2]octane, (+)-tartrate. Mp. 65–67° C. Compound 73.

(3S)3-(3-(1-(4-Fluorophenyl)-4-methyl-1-pentyn-3-yloxy)-1,2,5-thiadiazol-4-yl)-1-azabicyclo[2.2.2]octane, (+)-tartrate. Mp. 98–101° C. Compound 74.

(3S)3-(3-(3-(3,5-Dichlorophenyl)-2-propyn-1-yloxy)-1,2,5-thiadiazol-4-yl)-1-azabicyclo[2.2.2]octane, (+)-tartrate. Mp. 110–113° C. Compound 75.

(3S)3-(3-(3-(3-Bromophenyl)-2-propyn-1-yloxy)-1,2,5-thiadiazol-4-yl)-1-azabicyclo[2.2.2]octane, (+)-tartrate. Mp. 144–146° C. Compound 76.

(3S)3-(3-(3-(3-Trifluoromethoxyphenyl)-2-propyn-1-yloxy)-1,2,5-thiadiazol-4-yl)-1-azabicyclo[2.2.2]octane, (+)-tartrate. Mp. 123–125° C. Compound 77.

(3S)3-(3-(3-(3,5-Difluorophenyl)-2-propyn-1-yloxy)-1,2,5-thiadiazol-4-yl)-1-azabicyclo[2.2.2]octane, (+)-tartrate. Mp. 115–117° C. Compound 78.

(3S)3-(3-(3-(3-Chloro-5-fluorophenyl)-2-propyn-1-yloxy)-1,2,5-thiadiazol-4-yl)-1-azabicyclo[2.2.2]octane, (+)-tartrate. Mp. 116–118° C. Compound 79.

(3S)3-(3-(3-(3-Bromo-5-fluorophenyl)-2-propyn-1-yloxy)-1,2,5-thiadiazol-4-yl)-1-azabicyclo[2.2.2]octane, (+)-tartrate. Mp. 134–136° C. Compound 80.

(3S)3-(3-(3-(5-Chloro-2-thienyl)-2-propyn-1-yloxy)-1,2,5-thiadiazol-4-yl)-1-azabicyclo[2.2.2]octane, (+)-tartrate. Mp. 154–156° C. Compound 81.

EXAMPLE 8

Endo (5R,6S)-6-(3-(3-Phenyl-2-propyn-1-ylthio)-1,2,5-thiadiazol-4-yl)-1-azabicyclo[3.2.1]octane, (+)-tartrate Endo (5R,6S)-3-(3-propylsulfonyl-1,2,5-thiadiazol-4-yl)-1-azabicyclo[3.2.1]octane (WO 94/20496) (0.5 g, 1.66 mmol) and sodium hydrosulfide monohydrate (0.4 g, 5.3 mmol) were dissolved in dry DMF (50 ml) and the reaction mixture was refluxed at 100° C. for 3 hours (or to completion of reaction). After cooling to 0° C. potassium carbonate (0.9 g, 6.6 mmol) and 3-phenyl-2-propyn-1-yl methylsulfonate (1.0 g, 4.76 mmol) were added. The reaction mixture was stirred at room temperature for 4 hours (or to completion of reaction), after which 1N hydrogen chloride was added to pH 2. The aqueous phase was first washed with ether (2×50 ml), then potassium carbonate was added to pH>10 and finely the water phase was extracted with ether (2×100 ml). The combined and dried ether phases were evaporated and the residue (0.4 g) was crystallized with L-(+)-tartaric acid (0.2 g, 1.3 mmol) from isopropanol to give the title compound in 0.53 g yield (65%). Mp.171–173° C. Compound 20.

The following compounds were made in exactly the same manner using the appropriate methylsulfonate:

Endo (5R,6S)-6-(3-(3-(3-Fluorophenyl)-2-propyn-1-ylthio)-1,2,5-thiadiazol-4-yl)-1-azabicyclo[3.2.1]octane, (+)-tartrate. Mp. 138–140° C. Compound 21.

Endo (5R,6S)-6-(3-(3-(4-Fluorophenyl)-2-propyn-1-ylthio)-1,2,5-thiadiazol-4-yl)-1-azabicyclo[3.2.1]octane, (+)-tartrate. Mp. 198–199° C. Compound 22.

Endo (5R,6S)-6-(3-(3-(4-Chlorophenyl)-2-propyn-1-ylthio)-1,2,5-thiadiazol-4-yl)-1-azabicyclo[3.2.1]octane, (+)-tartrate. Mp. 190–192.5° C. Compound 23.

Endo (5R,6S)-6-(3-(3-(3-Thienyl)-2-propyn-1-ylthio)-1,2,5-thiadiazol-4-yl)-1-azabicyclo[3.2.1]octane, (+)-tartrate. Mp. 185–187° C. Compound 24.

Endo (5R,6S)-6-(3-(3-(2-Thienyl)-2-propyn-1-ylthio)-1,2,5-thiadiazol-4-yl)-1-azabicyclo[3.2.1]octane, (+)-tartrate. Mp. 187–189° C. Compound 25.

Endo (5R,6S)-6-(3-(3-(2-Fluorophenyl)-2-propyn-1-ylthio)-1,2,5-thiadiazol-4-yl)-1-azabicyclo[3.2.1]octane, (+)-tartrate. Mp. 149–152° C. Compound 82.

Endo (5R,6S)-6-(3-(3-(3-Methylthiophenyl)-2-propyn-1-ylthio)-1,2,5-thiadiazol-4-yl)-1-azabicyclo[3.2.1]octane, (+)-tartrate. Mp. 68–71° C. Compound 83.

Endo (5R,6S)-6-(3-(1-(3-Methoxyphenyl)-4-methyl-1-pentyn-3-ylthio)-1,2,5-thiadiazol-4-yl)-1-azabicyclo[3.2.1]octane, (+)-tartrate. Mp. 69–71° C. Compound 84.

Endo (5R,6S)-6-(3-(1-(3-Methoxyphenyl)-1-pentyn-3-ylthio)-1,2,5-thiadiazol-4-yl)-1-azabicyclo[3.2.1]octane, (+)-tartrate. Mp. 63–66° C. Compound 85.

Endo (5R,6S)-6-(3-(1-(2-Thienyl)-4-methyl-1-pentyn-3-ylthio)-1,2,5-thiadiazol-4-yl)-1-azabicyclo[3.2.1]octane, (+)-tartrate. Mp. 68–70° C. Compound 86.

Endo (5R,6S)-6-(3-(3-(3,5-Difluorophenyl)-2-propyn-1-ylthio)-1,2,5-thiadiazol-4-yl)-1-azabicyclo[3.2.1]octane, (+)-tartrate. Mp. 109–111° C. Compound 87.

EXAMPLE 9

Endo (5R,6S)-6-(3-(3-Phenyl-2-propyn-1-yloxy)-1,2,5-thiadiazol-4-yl)-1-azabicyclo[3.2.1]octane, (+)-tartrate To a mixture of sodium hydride (60% in mineral oil, 0.7 g, 17.5 mmol) in THF (50 ml) was added 3-phenyl-2-propyn-1-ol (0.74 g, 5.6 mmol) at room temperature and the reaction mixture was stirred for 1 hour. After cooling to 0° C., endo (5R,6S)-6-(3-propylsulfonyl-1,2,5-thiadiazol-4-yl)-1-azabicyclo[3.2.1]octane (WO 94/20496) (0.6 g, 2.0 mmol) was added. The reaction mixture was stirred for 5 hours at room temperature and at 5° C. overnight. Water (50 ml) was added and the mixture was extracted with ether (3×100 ml). The ether phases were evaporated and the residue was dissolved in 1N hydrochloric acid (20 ml). The water phase was washed with ether (100 ml), made basic with 25% aqueous ammonia and then extracted with ether (2×100 ml). The ether phases were dried and evaporated to give crude product (0.54 g). Purification on column chromatography eluting with ethyl acetate:methanol:25%aq.NH₃ (2:1:2%) gave the desired free base product as an oil. Crystallization with L-(+)-tartaric acid (0.27 g, 1.8 mmol) from isopropanol gave the title compound in 735 mg (77%) yield. Mp. 163–165° C. Compound 26.

The following compounds were made in exactly the same manner using the appropriate alcohol:

Endo (5R,6S)-6-(3-(3-(4-Fluorophenyl)-2-propyn-1-yloxy)-1,2,5-thiadiazol-4-yl)-1-azabicyclo[3.2.1]octane, (+)-tartrate. Mp. 147–149° C. Compound 27.

Endo (5R,6S)-6-(3-(3-(3-Methoxyphenyl)-2-propyn-1-yloxy)-1,2,5-thiadiazol-4-yl)-1-azabicyclo[3.2.1]octane, (+)-tartrate. Mp. 138–141° C. Compound 28.

Endo (5R,6S)-6-(3-(3-(4-Chlorophenyl)-2-propyn-1-yloxy)-1,2,5-thiadiazol-4-yl)-1-azabicyclo[3.2.1]octane, (+)-tartrate. Mp. 173–174° C. Compound 29.

Endo (5R,6S)-6-(3-[3-(3-Thienyl)-2-propyn-1-yloxy]-1,2,5-thiadiazol-4-yl)-1-azabicyclo[3.2.1]octane, (+)-tartrate. Mp. 158–160° C. Compound 30.

Endo (5R,6S)-6-(3-[3-(3-Pyridyl)-2-propyn-1-yloxy]-1,2,5-thiadiazol-4-yl)-1-azabicyclo[3.2.1]octane, (+)-tartrate. Mp. 136–139° C. Compound 31.

EXAMPLE 10

Endo (5S,6R)-6-(3-(3-Phenyl-2-propyn-1-yloxy)-1,2,5-thiadiazol-4-yl)-1-azabicyclo[3.2.1]octane, (+)-tartrate To a mixture of sodium hydride (60% in mineral oil, 0.6 g, 15 mmol) in THF (50ml) was added 3-phenyl-2-propyn-1-ol (0.62 g, 4.7 mmol) at room temperature and the reaction mixture was stirred for 1 hour. After cooling to 0° C., endo (5S,6R)-6-(3-propylsulfonyl-1,2,5-thiadiazol-4-yl)-1-azabicyclo[3.2.1]octane (WO 94/20496) (0.5 g, 1.66 mmol) was added. The reaction mixture was stirred for 5 hours at room temperature and at 5° C. overnight. Water (50 ml) was added and the mixture was extracted with ether (3×100 ml). The ether phases were evaporated and the residue was dissolved in 1N hydrochloric acid (20 ml). The water phase was washed with ether (100 ml), made basic with 25% aqueous ammonia and then extracted with ether (2×100 ml). The ether phases were dried and evaporated to give crude product (0.42 g). Purification on column chromatography eluting with ethyl acetate:methanol:25%aq.NH₃ (2:1:2%) gave the desired free base product as an oil. Crystallization with L-(+) tartaric acid (0.21 g, 1.4 mmol) from isopropanol gave the title compound in 350 mg (44%) yield. Mp. 155–161° C. Compound 32.

The following compounds were made in exactly the same manner using the appropriate alcohol and appropriate acid:

Endo (5S,6R)-6-(3-(3-(4-Fluorophenyl)-2-propyn-1-yloxy)-1,2,5-thiadiazol-4-yl)-1-azabicyclo[3.2.1]octane, (+)-tartrate. Mp. 164–165° C. Compound 33.

Endo (5S,6R)-6-(3-[3-(3-Methylthiophenyl)-2-propyn-1-yloxy]-1,2,5-thiadiazol-4)-1-azabicyclo[3.2.1]octane, (+)-tartrate. Mp. 77–79° C. Compound 34.

Endo (5S,6R)-6-(3-[1-(3-Methoxyphenyl)-4-methyl-1-pentyn-3-yloxy]-1,2,5-thiadiazol-4-yl)-1-azabicyclo[3.2.1]octane, (+)-tartrate. Mp. 72–74° C. Compound 35.

Endo (5S,6R)-6-(3-[3-(2,5-Difluorophenyl)-2-propyn-1-yloxy]-1,2,5-thiadiazol-4-yl)-1-azabicyclo[3.2.1]octane, (−)-tartrate. Mp. 167–169° C. Compound 36.

Endo (5S,6R)-6-(3-[3-(3,5-Difluorophenyl)-2-propyn-1-yloxy]-1,2,5-thiadiazol-4-yl)-1-azabicyclo[3.2.1]octane, (−)-tartrate. Mp. 154–156° C. Compound 37.

Endo (5S,6R)-6-(3-[1-(2-Thienyl)-4-methyl-1-pentyn-3-yloxy]-1,2,5-thiadiazol-4-yl)-1-azabicyclo[3.2.1]octane, (+)-tartrate. Mp. 80–82° C. Compound 38.

EXAMPLE 11

Exo (5R,6R)-6-(3-(3-Phenyl-2-propyn-1-ylthio)-1,2,5-thiadiazol-4-yl)-1-azabicyclo[3.2.1]octane, (+)-tartrate Exo (5R,6R)-3-(3-propylsulfonyl-1,2,5-thiadiazol-4-yl)-1-azabicyclo[3.2.1]octane (WO 94/20496) (0.43 g, 1.43 mmol) and sodium hydrosulfide monohydrate (0.28 g, 3.7 mmol) were dissolved in dry DMF (50 ml) and the reaction mixture was refluxed at 100° C. for 3 hours (or to completion of reaction). After cooling to 0° C. potassium carbonate (0.8 g, 5.7 mmol) and 3-phenyl-2-propyn-1-yl methylsulfonate (0.5 g, 2.5 mmol) were added. The reaction mixture was stirred at 0° C. for 4 hours (or to completion of reaction), after which 1N hydrogen chloride was added to pH 2. The aqueous phase was first washed with ether (2×50 ml), then potassium carbonate was added to pH>10 and finely the water phase was extracted with ether (2×100 ml). The combined and dried ether phases were evaporated and the residue (0.22 g) was crystallized with L-(+)-tartaric acid (0.1 g, 0.7 mmol) from isopropanol to give the title compound in 0.29 g yield (41%). Mp. 192–192.5° C. Compound 39.

The following compounds were made in exactly the same manner using the appropriate methylsulfonate:

Exo (5R,6R)-6-(3-(1-(3-Chlorophenyl)-4-methyl-1-pentyn-3-ylthio)-1,2,5-thiadiazol-4-yl)-1-azabicyclo[3.2.1]octane, (+)-tartrate. Mp.134–136° C. Compound 88.

Exo (5R,6R)-6-(3-(1-(3,5-Difluorophenyl)-4-methyl-1-pentyn-3-ylthio)-1,2,5-thiadiazol-4-yl)-1-azabicyclo[3.2.1]octane, (+)-tartrate. Mp.137–139° C. Compound 89.

Exo (5R,6R)-6-(3-(1-(3-Cyanophenyl)-4-methyl-1-pentyn-3-ylthio)-1,2,5-thiadiazol-4-yl)-1-azabicyclo[3.2.1]octane, (+)-tartrate. Mp.125–126° C. Compound 90.

Exo (5R,6R)-6-(3-(3-(3-Bromophenyl)-2-propyn-1-ylthio)-1,2,5-thiadiazol-4-yl)-1-azabicyclo[3.2.1]octane, (+)-tartrate. Mp.193–194° C. Compound 91.

Exo (5R,6R)-6-(3-(3-(3-Chloro-5-fluorophenyl)-2-propyn-1-ylthio)-1,2,5-thiadiazol-4-yl)-1-azabicyclo[3.2.1]octane, (+)-tartrate. Mp.166–168° C. Compound 92.

Exo (5R,6R)-6-(3-(3-(3-Bromo-5-fluorophenyl)-2-propyn-1-ylthio)-1,2,5-thiadiazol-4-yl)-1-azabicyclo[3.2.1]octane, (+)-tartrate. Mp.167–169° C. Compound 93.

Exo (5R,6R)-6-(3-(3-(5-Pyrimidyl)-2-propyn-1-ylthio)-1,2,5-thiadiazol-4-yl)-1-azabicyclo[3.2.1]octane, (+)-tartrate. Mp.147–148° C. Compound 94.

EXAMPLE 12

Exo (5R,6R)-6-(3-(3-Phenyl-2-propyn-1-yloxy)-1,2,5-thiadiazol-4-yl)-1-azabicyclo[3.2.1]octane, oxalate To a mixture of sodium hydride (60% in mineral oil, 0.6 g, 15 mmol) in THF (50ml) was added 3-phenyl-2-propyn-1-ol (0.62 g, 4.7 mmol) at room temperature and the reaction mixture was stirred for 1 hour. After cooling to 0° C., exo (5R,6R)6-(3-propylsulfonyl-1,2,5-thiadiazol-4-yl)-1-azabicyclo[3.2.1]octane (WO 94/20496) (0.5 g, 1.66 mmol) was added. The reaction mixture was stirred for 5 hours at room temperature and at 5° C. overnight. Water (50 ml) was added and the mixture was extracted with ether (3×100 ml). The ether phases were evaporated and the residue was dissolved in 1N hydrochloric acid (20 ml). The water phase was washed with ether (100 ml), made basic with 25% aqueous ammonia and then extracted with ether (2×100 ml). The ether phases were dried and evaporated to give crude product. Purification on column chromatography eluting with ethyl acetate:methanol:25%aq.NH$_3$ (2:1:2%) gave the desired free base product as an oil. Crystallization with oxalic acid gave the title compound in 560 mg (78%) yield. Mp. 120–125° C. Compound 40.

The following compounds were made in the same manner using the appropriate alcohol and appropriate acid:

Exo (5R,6R)-6-(3-(3-(3-Methoxyphenyl)-2-propyn-1-yloxy)-1,2,5-thiadiazol-4-yl)-1-azabicyclo[3.2.1]octane, oxalate. Mp. 116–117.5° C. Compound 41.

Exo (5R,6R)-6-(3-(3-(3-Trifluoromethylphenyl)-2-propyn-1-yloxy)-1,2,5-thiadiazol-4-yl)-1-azabicyclo[3.2.1]octane, (+)-tartrate. Mp. 109–115° C. Compound 42.

Exo (5R,6R)-6-(3-(3-(3-Methoxyphenyl)-1-methyl-2-propyn-1-yloxy)-1,2,5-thiadiazol-4-yl)-1-azabicyclo[3.2.1]octane, (+)-tartrate. Mp. 134.5–136.5° C. Compound 43.

Exo (5R,6R)-6-(3-(3-(4-Chlorophenyl)-2-propyn-1-yloxy)-1,2,5-thiadiazol-4-yl)-1-azabicyclo[3.2.1]octane, (+)-tartrate. Mp. 188–190° C. Compound 44.

Exo (5R,6R)-6-(3-(1-(3-Methoxyphenyl)-4-methyl-1-pentyn-3-yloxy)-1,2,5-thiadiazol-4-yl)-1-azabicyclo[3.2.1]octane, (+)-tartrate. Mp. 153–156° C. Compound 45.

Exo (5R,6R)-6-(3-(1-(4-Chlorophenyl)-4-methyl-1-pentyn-3-yloxy)-1,2,5-thiadiazol-4-yl)-1-azabicyclo[3.2.1]octane, (+)-tartrate. Mp. 154–157.5° C. Compound 46.

Exo (5R,6R)-6-(3-(3-(2-Thienyl)-1-methyl-2-propyn-1-yloxy)-1,2,5-thiadiazol-4-yl)-1-azabicyclo[3.2.1]octane, (+)-tartrate. Mp. 150–151° C. Compound 47.

Exo (5R,6R)-6-(3-(3-(3-Thienyl)-1-methyl-2-propyn-1-yloxy)-1,2,5-thiadiazol-4-yl)-1-azabicyclo[3.2.1]octane, (+)-tartrate. Mp. 146.5–147.5° C. Compound 48.

Exo (5R,6R)-6-(3-[3-(2-Thienyl)-2-propyn-1-yloxy]-1,2,5-thiadiazol-4-yl)-1-azabicyclo[3.2.1]octane, oxalate. Mp. 137–139° C. Compound 49.

Exo (5R,6R)-6-(3-[3-(3-Thienyl)-2-propyn-1-yloxy]-1,2,5-thiadiazol-4-yl)-1-azabicyclo[3.2.1]octane, oxalate. Mp. 131–132° C. Compound 50.

Exo (5R,6R)-6-(3-(1-(3-Thienyl)-4-methyl-1-pentyn-3-yloxy)-1,2,5-thiadiazol-4-yl)-1-azabicyclo[3.2.1]octane, (+)-tartrate. Mp. 145–148° C. Compound 51.

Exo (5R,6R)-6-(3-(4-methyl-1-phenyl-1-pentyn-3-yloxy)-1,2,5-thiadiazol-4-yl)-1-azabicyclo[3.2.1]octane, (+)-tartrate. Mp. 146–148° C. Compound 95.

Exo (5R,6R)-6-(3-(1-(3,5-Dichlorophenyl)-4-methyl-1-pentyn-3-yloxy)-1,2,5-thiadiazol-4-yl)-1-azabicyclo[3.2.1]octane, (+)-tartrate. Mp. 180–182° C. Compound 96.

Exo (5R,6R)-6-(3-(3-(3-Cyanophenyl)-2-propyn-1-yloxy)-1,2,5-thiadiazol-4-yl)-1-azabicyclo[3.2.1]octane, (+)-tartrate. Mp. 136–138° C. Compound 97.

Exo (5R,6R)-6-(3-(1-(3-Chlorophenyl)-4-methyl-1-pentyn-3-yloxy)-1,2,5-thiadiazol-4-yl)-1-azabicyclo[3.2.1]octane, (+)-tartrate. Mp. 157–159° C. Compound 98.

Exo (5R,6R)-6-(3-(1-(3-Cyanophenyl)-4-methyl-1-pentyn-3-yloxy)-1,2,5-thiadiazol-4-yl)-1-azabicyclo[3.2.1]octane, (+)-tartrate. Mp. 160–162° C. Compound 99.

Exo (5R,6R)-6-(3-(1-(3,5-Difluorophenyl)-4-methyl-1-pentyn-3-yloxy)-1,2,5-thiadiazol-4-yl)-1-azabicyclo[3.2.1]octane, (+)-tartrate. Mp. 185–187° C. Compound 100.

Exo (5R,6R)-6-(3-(3-(3,5-Difluorophenyl)-2-propyn-1-yloxy)-1,2,5-thiadiazol-4-yl)-1-azabicyclo[3.2.1]octane, (+)-tartrate. Mp. 138–140° C. Compound 101.

Exo (5R,6R)-6-(3-(3-(3-Bromophenyl)-2-propyn-1-yloxy)-1,2,5-thiadiazol-4-yl)-1-azabicyclo[3.2.1]octane, (+)-tartrate. Mp. 171–173° C. Compound 102.

Exo (5R,6R)-6-(3-(3-(3-Chloro-5-fluorophenyl)-2-propyn-1-yloxy)-1,2,5-thiadiazol-4-yl)-1-azabicyclo[3.2.1]octane, (+)-tartrate. Mp. 167–168° C. Compound 103.

Exo (5R,6R)-6-(3-(3-(3-Bromo-5-fluorophenyl)-2-propyn-1-yloxy)-1,2,5-thiadiazol-4-yl)-1-azabicyclo[3.2.1]octane, (+)-tartrate. Mp. 162–163° C. Compound 104.

Exo (5R,6R)-6-(3-(1-(2-Thienyl)-4-methyl-1-pentyn-3-yloxy)-1,2,5-thiadiazol-4-azabicyclo[3.2.1]octane, (+)-tartrate. Mp. 135–137° C. Compound 105.

Exo (5R,6R)-6-(3-(3-(3-Furyl)-2-propyn-1-yloxy)-1,2,5-thiadiazol-4-yl)-1-azabicyclo[3.2.1]octane, (+)-tartrate. Mp. 160–161° C. Compound 106.

EXAMPLE 13

Exo (5S,6S)-6-(3-(3-Phenyl-2-propyn-1-yloxy)-1,2,5-thiadiazol-4-yl)-1-azabicyclo[3.2.1]octane, oxalate To a mixture of sodium hydride (60% in mineral oil, 0.6 g, 15 mmol) in THF (50 ml) was added 3-phenyl-2-propyn- 1-ol (0.62 g, 4.7 mmol) at room temperature and the reaction mixture was stirred for 1 hour. After cooling to 0° C., exo (5S,6S)-6-(3-propylsulfonyl-1,2,5-thiadiazol-4-yl)-1-azabicyclo[3.2.1]octane (WO 94/20496) (0.5 g, 1.66 mmol) was added. The reaction mixture was stirred for 5 hours at room temperature and at 5° C. overnight. Water (50 ml) was added and the mixture was extracted with ether (3×100 ml). The ether phases were evaporated and the residue was dissolved in 1N hydrochloric acid (20 ml). The water phase was washed with ether (100 ml), made basic with 25% aqueous ammonia and then extracted with ether (2×100 ml). The ether phases were dried and evaporated to give crude product. Purification on column chromatography eluting with ethyl acetate:methanol:25%aq.NH$_3$ (2:1:2%) gave the desired free base product as an oil. Crystallization with oxalic acid gave the title compound in 520 mg (72%) yield. Mp.132–135° C. Compound 52.

EXAMPLE 14

(+−) 3-(3-(3-Phenyl-2-propyn-1-yloxy)-1,2,5-thiadiazol4-yl)-1-azabicyclo[2.2.2]octane, oxalate To a solution of 3-phenyl-2-propyn-1-ol (3.0 g, 15 mmol) in THF (20 ml) was added sodium hydride (80% in mineral oil, 0.45 g, 15 mmol). The reaction mixture was stirred at room temperature for 1 hour and then a solution of (+−) 3-(3-chloro-1,2,5-thiadiazol-4-yl)-1-azabicyclo[2.2.2] octane (Eur. J. Med. Chem., 1996, 31, 221–230) (1.15 g, 5 mmol) in THF (15 ml) was added. The reaction mixture was stirred at 50° C. for 18 hours. 1N hydrogen chloride was added and the THF phase was discharged. The water phase was made basic with sodium hydroxide and then extracted with ether (3×100 ml). The combined ether phases were dried and evaporated to give crude product. The residue was purified by column chromatography eluting with ethyl acetate:methanol:25%aq.NH$_3$ (80:20:0.5). Crystallization with oxalic acid from acetone gave the title compound in 310 mg (15%) yield. Mp. 91–94° C. Compound 53.

The following compound was made in exactly the same manner using the appropriate alcohol:
(+−) 3-(3-(3-(4-Fluorophenyl)-2-propyn-1-yloxy)-1,2,5-thiadiazol-4-yl)-1-azabicyclo[2.2.2]octane, oxalate. Mp. 102–103° C. Compound 54.

EXAMPLE 15

(+−) 3-(3-(3-(4-Chlorophenyl)-2-propyn-1-ylthio)-1,2,5-thiadiazol-4-yl)-1-azabicyclo[2.2.2]octane, (+)-tartrate To a solution of (+−) 3-(3-chloro-1,2,5-thiadiazol-4-yl)-1-azabicyclo[2.2.2]octane (Eur. J. Med. Chem., 1996, 31, 221–230) (0.8 g, 3.5 mmol) in DMF (20 ml) was added sodium hydrosulfide monohydrate (0.66 g, 8 mmol). The reaction mixture was stirred at room temperature for 5 hours. Potassium carbonate (1.38 g, 10 mmol) and 3-(4-chlorophenyl)-2-propyn-1-yl methylsulfonate (0.87 g, 3.5 mmol) was added. The reaction mixture was stirred at room temperature over night. 1 N hydrochloric acid was added and the mixture was washed with ether (100 ml). The water phase was made basic with potassium carbonate and extracted with ether (3×100 ml). The combined ether phases were dried and evaporated to give crude product (1.22 g). Crystallization with L-(+)tartaric acid from isopropanol followed by recrystallisation from acetone-isopropanol gave the title compound in 960 mg (52%) yield. Mp. 184–185° C. Compound 55.

The following compound was made in the same manner using the appropriate methylsulfonate:
(+−) 3-(3-(3-(3-Chlorophenyl)-2-propyn-1-ylthio)-1,2,5-thiadiazol-4-yl)-1-azabicyclo[2.2.2]octane, (+)-tartrate. Mp. 168–170° C. Compound 111.

EXAMPLE 16

Endo (β) 3-(3-(3-(3.5-Difluorophenyl)-2-propyn-1-ylthio)-1,2,5-thiadiazol-4-yl)-1-azabicyclo[2.2.1] heptane, (−)-tartrate Endo (−) 3-(3-(3-propylsulfonyl-1,2,5-thiadiazol-4-yl)-1-azabicyclo[2.2.1]heptane (W094/20496) (1.5 g, 5.2 mmol) and potassium carbonate (1.4 g, 10.4 mmol) in dry DMF(20 ml) was added sodium hydrosulfide monohydrate (1.15 g, 15.6 mmol). The reaction mixture was heated to 70° C. During this period another two portions of sodium hydrosulfide monohydrate was added to complete the reaction. DMF was evaporated and the residue added ice water followed by 4 N hydrochloric acid to pH 8–9. The product was isolated by filtration to give 862 mg (78%) of Endo (β) 4-(1-azabicyclo[2.2.1]hept-3-yl)-1,2,5-thiadiazol-3-thiol.

To a suspension of endo (β)-4-(1-azabicyclo[2.2.1]hept-3-yl)-1,2,5-thiadiazol-3-thiol (107 mg, 0.5 mmol) and potassium carbonate (123 mg, 0.5 mmol) in dry THF (10 ml) cooled on ice was under nitrogen added a solution of 3-(3,5-difluorophenyl)-2-propyn-1-yl methylsulfonate (123 mg, 0.5 mmol) in dry THF (5 ml). The reaction mixture was stirred overnight and the temperature allowed to raise to room temperature. Ice water was added and pH adjusted with 1 N hydrochloric acid to pH 2.0. THF was evaporated and the residue washed with ether (3×50 ml). The water phase was made basic with 25% aqueous ammonia (pH 10–11) and the product extracted with ether (3×50 ml). The dried ether phases were evaporated and the residue crystallised with D-(−)-tartaric acid in isopropanole. The title compound was isolated by filtration in 100 mg yield (40%). Mp. 142–144° C. Compound 107.

The following compound was made in the same manner using the appropriate methylsulfonate:
Endo (β) 3-(3-(3-(3-Fluorophenyl)-2-propyn-1-ylthio)-1,2, 5-thiadiazol-4-yl)-1-azabicyclo[2.2.1]heptane, (−)-tartrate. Mp. 170–171° C. Compound 108.

EXAMPLE 17

Endo (β) 3-(3-(3-(3-Chloro-5-fluorophenyl)-2-propyn-1-ylthio)-1,2,5-thiadiazol-4-yl)-1-azabicyclo[2.2.1] heptane, (−)-tartrate To an ice cooled suspension of endo (β)-4-(1-azabicyclo [2.2.1]hept-3-yl)-1,2,5-thiadiazol-3-thiol (described in example 16) (213 mg, 1.0 mmol) and triphenylphosphine (262 mg, 1.0 mmol) in dry THF (10 ml) was under nitrogen added 3-(3-chloro-5-fluorophenyl)-prop-2-yn-1-ol (277 mg, 1.5 mmol) in THF (5 ml). Diethyl azodicarboxylate (174 mg, 1.0 mmol) was added and the temperature allowed to raise to room temperature while stirring overnight. Ice water was added and pH adjusted with 4 N hydrochloric acid (pH 2.0). THF was evaporated and the water phase washed with ether (2×75 ml). 25% Aqueous ammonia was added (pH 10–11) and the product extracted by ether (3×75 ml). The dried ether phases were evaporated and the residue crystallised with D-(−)-tartaric acid in isopropanole. The title compound was isolated by filtration in 245 mg yield (46%). Mp. 68–70° C. Compound 109.

The following compound was made in the same manner using the appropriate alcohol:

Endo (β) 3-(3-(3-(3-Bromo-5-fluorophenyl)-2-propyn-1-ylthio)-1,2,5-thiadiazol-4-yl)-1-azabicyclo[2.2.1]heptane, (−)-tartrate. Mp. 81–82° C. Compound 110.

EXAMPLE 18

(3S) 3-(3-(3-(3-Fluorophenyl)-2-propyn-1-ylthio)-1,2,5-thiadiazol-4-yl)-1-azabicyclo[2.2.2]octane, (+)-tartrate To a solution of (3S) 3-(3-butylsulfonyl-1,2,5-thiadiazol-4-yl)-1-azabicyclo[2.2.2]octane (Chirality, 1997, in press.) (1.90 g, 6.0 mmol) in dry DMF (15 ml) was added sodium hydrosulfide monohydrate (1.67 g, 18.0 mmol) and the mixture was stirred at 95° C. for 3 h. The reaction mixture was concentrated in vacuo, added ice water and made less basic with 4 N hydrochloride acid. The precipitate was isolated by filtration to give 1.05 g (77%) of (3S)3-(3-mercapto-1,2,5-thiadiazol-4-yl)-1-azabicyclo[2.2.2]octane.

To an ice cooled suspension of (3S) 3-(3-mercapto-1,2,5-thiadiazol-4-yl)-1-azabicyclo[2.2.2]octane (340 mg, 1.5 mmol) and triphenylphosphine (390 mg, 1.5 mmol) in dry THF (30 ml) was under nitrogen added 3-(4-fluorophenyl)-prop-2-yn-1-ol (350 mg, 2.3 mmol) in dry THF (25 ml) followed by diethyl azodicarboxylate (260 mg, 1.5 mmol). After stirring at room temperature for 48 h the mixture was concentrated in vacuo and the residue submitted to flash chromatography using methanol/ethyl acetate (1:4) graduated to methanol/ethyl acetate/ammonium hydroxide (1:3:3%) as the eluent. The purified product was crystallised with L-(+)-tartaric acid in isopropanol to give 440 mg (86%) of the title compound. Mp. 174–175° C. Compound 112.

The following compounds were made in the same manner using the appropriate alcohol:

(3S) 3-(3-(3-(3,5-Dichlorophenyl)-2-propyn-1-ylthio)-1,2,5-thiadiazol-4-yl)-1-azabicyclo[2.2.2]octane, (+)-tartrate. Mp. 103–105° C. Compound 113.

(3S) 3-(3-(3-(3-Bromophenyl)-2-propyn-1-ylthio)-1,2,5-thiadiazol-4-yl)-1-azabicyclo[2.2.2]octane, (+)-tartrate. Mp. 175–176° C. Compound 114.

(3S) 3-(3-(3-(3-Trifluoromethoxyphenyl)-2-propyn-1-ylthio)-1,2,5-thiadiazol-4-yl)-1-azabicyclo[2.2.2]octane, (+)-tartrate. Mp. 153–155° C. Compound 115.

(3S) 3-(3-1-(3,5-Difluorophenyl)-4-methyl-1-pentyn-3-ylthio)-1,2,5-thiadiazol-4-yl)-1-azabicyclo[2.2.2]octane, (+)-tartrate. Mp. 146–148° C. Compound 116.

(3S) 3-(3-(3-(3,5-Difluorophenyl)-2-propyn-1-ylthio)-1,2,5-thiadiazol-4-yl)-1-azabicyclo[2.2.2]octane, (+)-tartrate. Mp. 130–133° C. Compound 117.

(3S) 3-(3-(3-(3-Bromo-5-fluorophenyl)-2-propyn-1-ylthio)-1,2,5-thiadiazol-4-yl)-1-azabicyclo[2.2.2]octane, (+)-tartrate. Mp. 113–115° C. Compound 118.

(3S) 3-(3-(3-(5-Chloro-2-thienyl)-2-propyn-1-ylthio)-1,2,5-thiadiazol-4-yl)1-azabicyclo[2.2.2]octane, (+)-tartrate. Mp. 164–167° C. Compound 119.

We claim:

1. A compound of formula I

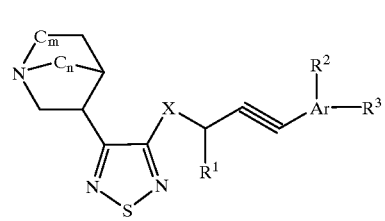

(I)

wherein

X is oxygen or sulphur; and $R^1$ is hydrogen, straight or branched $C_{1-5}$-alkyl, straight or branched $C_{2-5}$-alkenyl, straight or branched $C_{2-5}$-alkenyl or straight or branched $C_{4-5}$-alkenynyl, each of which is optionally substituted with a halogen; and $R^2$ and $R^3$ are independently hydrogen, halogen, CN, $NO_2$, $CF_3$, $OCF_3$, $C_{1-3}$-alkyl, $C_{1-3}$-alkoxy or $C_{1-3}$-alkylthio, wherein $C_{1-3}$-alkyl, $C_{1-3}$-alkoxy and $C_{1-3}$-alkylthio are optionally substituted with a halogen, cyano, amino or nitro; and Ar is pyrimidinyl or furyl; and n is 1 or 2; and m is 1 or 2; or a pharmaceutically acceptable salt thereof.

2. A compound of claim 1 wherein $R^1$ is straight or branched $C_{1-3}$-alkyl.

3. A compound of claim 2 wherein $R^1$ is isopropyl.

4. A compound of claim 1 wherein $R^2$ and $R^3$ are halogen.

5. A compound of claim 1 wherein X is sulfur.

6. A compound of claim 5 wherein $R^1$ is hydrogen.

7. A compound of claim 5 wherein $R^2$ and $R^3$ are hydrogen.

8. A compound of claim 5 wherein Ar is pyrimidinyl.

9. A compound of claim 5 wherein m is 1 and n is 2.

10. A compound of claim 5 wherein m is 2 and n is 1.

11. A compound of claim 5 wherein m is 1 and n is 1.

12. A compound of claim 1 wherein X is oxygen.

13. A compound of claim 12 wherein $R^1$ is hydrogen.

14. A compound of claim 12 wherein $R^2$ and $R^3$ are hydrogen.

15. A compound of claim 12 wherein Ar is furyl.

16. A compound of claim 12 wherein m is 1 and n is 2.

17. A compound of claim 12 wherein m is 2 and n is 1.

18. A compound of claim 12 wherein m is 1 and n is 1.

19. A compound of claim 1 which is:

Endo (β)-3-(3-(3-(3-Furyl)-2-propyn-1-yloxy)-1,2,5-thiadiazol-4-yl)-1-azabicyclo[2.2.1]heptane;

Exo (5R,6R)-6-(3-(3-(3-Furyl)-2-propyn-1-yloxy)-1,2,5-thiadiazol-4-yl)-1-azabicyclo[3.2.1]octane; or a pharmaceutically acceptable salt thereof.

20. A compound of claim 1 which is:

Exo (5R,6R)-6-(3-(3-(5-Pyrimidyl)-2-propyn-1-ylthio)-1,2,5-thiadiazol-4-yl)-1-azabicyclo[3.2.1]octane; or a pharmaceutically acceptable salt thereof.

21. A pharmaceutical composition comprising a compound of claim 1 together with a pharmaceutically acceptable carrier or diluent.

22. The pharmaceutical composition of claim 21 in the form of an oral dosage unit or parenteral dosage unit.

23. The pharmaceutical composition of claim 22, wherein said dosage unit comprises from about 0.1 to about 100 mg.

* * * * *